United States Patent [19]

Shankar et al.

[11] Patent Number: 5,006,656

[45] Date of Patent: Apr. 9, 1991

[54] PREPARATION OF 5,7-DIHYDROXY-1,2,4-TRIAZOLO[1,5-A]PYRIMIDINE-2-SULFONANILIDES

[75] Inventors: Ravi B. Shankar; R. Garth Pews, both of Midland, Mich.

[73] Assignee: DowElanco, Indianapolis, Ind.

[21] Appl. No.: 484,960

[22] Filed: Feb. 26, 1990

[51] Int. Cl.$^5$ .............................................. C07D 403/14
[52] U.S. Cl. ............................................................ 544/263
[58] Field of Search .......................................... 544/263

[56] References Cited

U.S. PATENT DOCUMENTS

| | | | |
|---|---|---|---|
| 4,734,123 | 3/1988 | Monte | 544/263 |
| 4,818,273 | 4/1989 | Kleschick et al. | 544/263 |
| 4,822,404 | 4/1989 | Kleschick | 544/263 |
| 4,904,301 | 2/1990 | Pearson et al. | 544/263 |

FOREIGN PATENT DOCUMENTS 0255735  4/1988  German Democratic Rep. ................... 544/263

*Primary Examiner*—Donald G. Daus
*Attorney, Agent, or Firm*—Craig E. Mixan; Ronald G. Brookens

[57] ABSTRACT

5,7-Dihydroxy-N-(aryl)-1,2,4-triazolo[1,5-a]pyrimidine-2-sulfonamides are prepared by the cyclization of N-(3-(((aryl)amino)sulfonyl)-1H-1,2,4-triazol-5-yl)amines with malonyl halides under acidic conditions. With the addition of a phosphorus oxyhalide, malonic acid can be used in place of the malonyl halides and the 5,7-dihydroxy-1,2,4-triazolo[1,5-a]pyrimidine can be directly converted to the corresponding 5,7-dihalo derivative.

10 Claims, No Drawings

PREPARATION OF 5,7-DIHYDROXY-1,2,4-TRIAZOLO[1,5-A]PYRIMIDINE-2-SULFONANILIDES

FIELD OF THE INVENTION

The present invention relates to a process for the preparation of 5,7-dihydroxy-N-(aryl)-1,2,4-triazolo1,5-a]pyrimidine-2-sulfonamides by the cyclization of N-(3-(((aryl)amino)sulfonyl)-1H-1,2,4-triazol-5-yl)amines with malonyl halides. With the addition of a phosphorus oxyhalide, malonic acid can be used in place of the malonyl halides and the 5,7-dihydroxy-1,2,4-triazolo[1,5-a]pyrimidine-2-sulfonanilide can be directly converted to the corresponding 5,7-dihalo analog.

BACKGROUND OF THE INVENTION

Substituted 1,2,4-triazolo[1,5-a]pyrimidine-2-sulfonanilides (I)

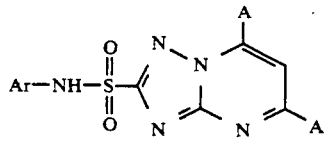

are valuable herbicides for the selective control of weeds in agronomic crops. Among the more valuable herbicides of formula (I) are those described in U.S. Pat. No. 4,818,273 in which the substituents A are both either halo, hydroxy or alkoxy. Compounds of this family have generally been prepared via the intermediacy of the 5,7-dihydroxy compounds. For example, the dihydroxy compounds can be halogenated to the 5,7-dihalo analogs, which in turn can be reacted with alkoxides to provide the corresponding 5,7-dialkoxy compounds.

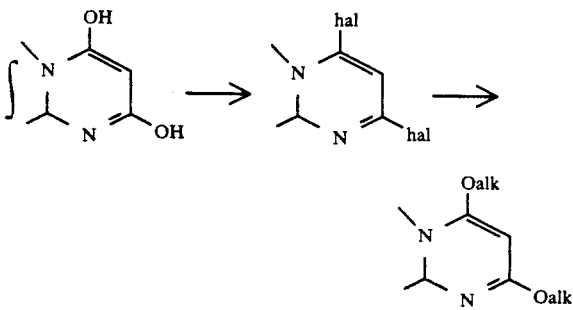

The 5,7-dihydroxy compounds have been disclosed as being prepared by the cyclization of N-(3-(((aryl)amino)sulfonyl)-1H-1,2,4-triazol-5-yl)amines (II) with dialkyl malonates in the presence of sodium alkoxide in alcohol followed by acidification of the intermediate trisodium salt (III).

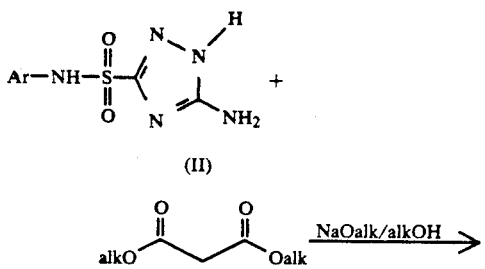

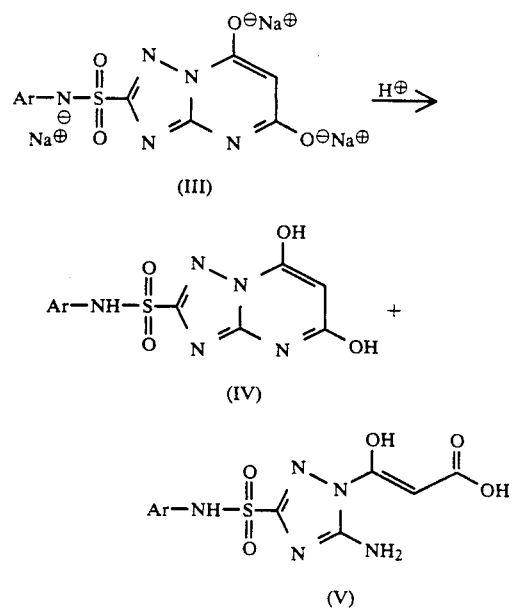

This process has the following disadvantages:
(1) the reaction time for the cyclization is generally 24 to 48 hours (hr);
(2) the process requires 3 equivalents of expensive sodium alkoxide base;
(3) on acidification, the intermediate trisodium salt (III) yields approximately 5 to 25 percent ring-opened product (V) which can be lost during the isolation of the desired product (IV); and
(4) the neutralization process requires 3 equivalents of acid and generates considerable quantities of waste brine.

In view of the valuable herbicidal properties of the sulfonamides (I), it is desirable to have a process for the preparation of N-(aryl)-5,7-dihydroxy-1,2,4-triazolo[1,5-a]pyrimidine-2-sulfonamides which avoids unnecessary yield loss. It is also desirable to have a process that eliminates the sodium alkoxide base, does not generate large amounts of waste brine, and does not require protracted reaction times.

SUMMARY OF THE INVENTION

The present invention relates to a process for the preparation of N-(aryl)-5,7-dihydroxy-1,2,4-triazolo[1,5-a]pyrimidine-2-sulfonamides of the formula:

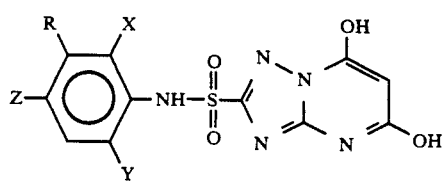

wherein
X represents H, F, Cl, Br, lower alkyl or lower alkoxy,
Y represents H, F, Cl, Br, $CF_3$ or $NO_2$,
R represents H, lower alkyl or lower alkoxy, and
Z represents H, Cl or Br,
which comprises contacting an N-(3-(((aryl)amino)-sulfonyl)-1H-1,2,4-triazol-5-yl)amine of the formula:

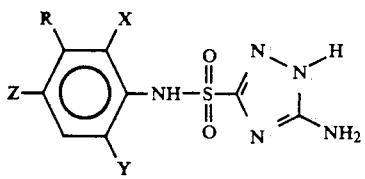

wherein
X, Y, R and Z are as previously defined,
with a malonyl halide under acidic conditions in a polar aprotic solvent.

By conducting the reaction in the presence of a phosphorus oxyhalide, malonic acid can be substituted for the malonyl halide and the 5,7-dihydroxy-1,2,4-triazolo[1,5-a]pyrimidine-2-sulfonanilide can be directly converted to the corresponding 5,7-dihalo analog. Alternatively, the 5,7-dihalo derivatives can be prepared by subsequent treatment of the cyclization reaction mixture with a phosphorus oxyhalide.

The present invention has the advantage of being able to prepare 5,7-dihydroxy-1,2,4-triazolo-[1,5-a]pyrimidine-2-sulfonanilides in a one step process without using any base. By avoiding an acidification step, yield losses are greatly reduced. Similarly, the generation of a waste brine is eliminated. And, finally, a subsequent halogenation step can be combined with the cyclization step to simplify the overall process for preparing the corresponding 5,7-dihalo derivatives.

DETAILED DESCRIPTION OF THE INVENTION

As used herein, the terms "lower alkyl" and "lower alkoxy" are meant to designate straight or branched, saturated alkyl or alkoxy groups of from 1 to 4 carbon atoms.

Where individual members of the halogen family are not specifically listed, the general terms "halogen", "halide", "halo" and "hal", as used herein, are meant to be construed as being limited to chloro and bromo.

Malonyl halides are commercially available starting materials. Because of its lesser expense and more ready availability, malonyl chloride is preferred over the bromide. The malonyl halide is preferably freshly distilled prior to use.

The N-(3-(((aryl)amino)sulfonyl)-1H-1,2,4-triazol-5-yl)amines are known compounds and are described in U.S. Pat. No. 4,734,123. Of these starting materials, X and Y are preferably H, F or Cl. Z is preferably H or Br. For R, the preferred "lower alkyl" and "lower alkoxy" groups are —CH$_3$, —CH$_2$CH$_3$, —OCH$_3$ and —OCH$_2$CH$_3$. The most preferred group is —CH$_3$.

In the cyclization reaction, the N-(3-(((aryl)amino)sulfonyl)-1H-1,2,4-triazol-5-yl)amine is condensed with the malonyl halide. In principal, one equivalent of each reagent is required: in practice, a slight excess of the malonyl halide is preferred. Generally, from 1.0 to 2.0 equivalents of the malonyl halide are employed, while 1.0 to 1.2 equivalents are preferred.

By conducting the reaction "under acidic conditions" is meant under conditions wherein no salts in which the product comprises the anionic component are formed. In the basic condensations of the prior art, the trisodium salts (III) are formed as reaction intermediates which must be neutralized with acid to provide the desired products (IV). The present invention envisions the avoidance of such salts as intermediates. Since hydrogen halide is a by-product of the instant process, the reaction conditions are inherently acidic.

The cyclization reaction is preferably carried out in the presence of a dry polar aprotic solvent which is inert to the reaction conditions. Preferred solvents include but are not limited to alkylnitriles, such as, for example, acetonitrile or butyronitrile; ethers, such as, for example, tetrahydrofuran or dioxane: and carboxylic acid esters, such as, for example, ethyl acetate. The solvents are preferably freshly distilled and dried prior to use.

The cyclization reaction with malonyl halide is generally run from about room temperature to about 100° C., preferably from ambient temperature to about 50° C.

The cyclization reaction is optionally conducted under an inert atmosphere, such as, for example, under a nitrogen or argon blanket. Although conveniently conducted at atmospheric pressure, the reaction is preferably run under a slight positive nitrogen pressure of up to about 5 pounds per square inch gauge pressure (psig) which helps in keeping out undesirable atmospheric moisture.

In a typical reaction, the N-(3-(((aryl)amino)sulfonyl)-1H-1,2,4-triazol-5-yl)amine is dissolved in a dry polar aprotic solvent and is stirred with about one equivalent of freshly distilled malonyl halide. After completion of the reaction, usually in from about 8 to about 24 hr, the 5,7-dihydroxy compound can be recovered by conventional techniques, e.g., by filtration, by extraction or by recrystallization.

Optionally, the malonyl halide may be replaced with malonic acid and with the corresponding phosphorus oxyhalide At least 2 equivalents of phosphorus oxyhalide are required for each equivalent of malonic acid. It is often convenient to use a large excess of the phosphorus oxyhalide. By a large excess is meant from 2 up to 10 equivalents and more over that required by the ideal stoichiometry. When a large excess of phosphorus oxyhalide is employed, the polar aprotic organic solvent can be optionally removed, being effectively replaced by the phosphorus oxyhalide. When using malonic acid and the phosphorus oxyhalide in place of the malonyl halide, the reaction is preferably conducted between about 70° and about 90° C.

If the 5,7-dihalo-1,2,4-triazolo1,5-a]pyrimidine-2-sulfonanilides are desired, the 5,7-dihydroxy compounds can be contacted with a sufficient quantity of phosphorus oxyhalide. One equivalent of phosphorus oxyhalide is required for each hydroxy group to be replaced. Thus, at least two equivalents of phosphorus oxyhalide are typically employed to convert the 5,7-dihydroxy compounds to their corresponding 5,7-dihalo counterparts. It is often most convenient to use a large excess of the phosphorus oxyhalide which can be added concurrently with the malonyl halide prior to cyclization or which can be added to the reaction mixture after cyclization.

In the most preferred embodiment, the 5,7-dihalo-1,2,4-triazolo[1,5-a]pyrimidine-2-sulfonanilides are prepared directly from the N-(3-(((aryl)amino)sulfonyl)-1H-1,2,4-triazol-5-yl)amines by conducting the cyclization and halogenation reactions consecutively by using at least one equivalent of malonic acid and at least 4 equivalents of phosphorus oxyhalide concurrently. Stoichiometric excesses of both reagents are often beneficially employed. The reaction is preferably conducted between about 70° and about 100° C.

In some cases, it is helpful to employ a tertiary amine, such as, for example, dimethyl aniline, as a catalyst for the reaction. In those cases where the use of the catalyst is beneficial, the tertiary amine is generally employed at levels in the range of about 0.1 to about 40 mole percent of the N-(3-(((aryl)amino)sulfonyl)-1H-1,2,4-triazol-5-yl)amine starting material, more preferably in the range of about 1 to about 20 mole percent.

In a typical reaction, the N-(3-(((aryl)amino)sulfonyl)-1H-1,2,4-triazol-5-yl)amine, about one equivalent of malonic acid and a large excess of phosphorus oxyhalide are heated with stirring. After the reaction is complete, the 5,7-dihalo compound can be recovered by conventional techniques. For example, the reaction mixture can be cooled and carefully diluted with water, and the product can be isolated by filtration, by extraction or the like.

The following examples are presented to illustrate the invention and should not be construed as limiting the scope of the invention. All melting points are uncorrected.

EXAMPLE 1

Preparation of 5,7-Dihydroxy-N-(2 6-dichloro-3-methylphenyl)-1,2,4-triazolo[1,5-a]pyrimidine-2-sulfonamide

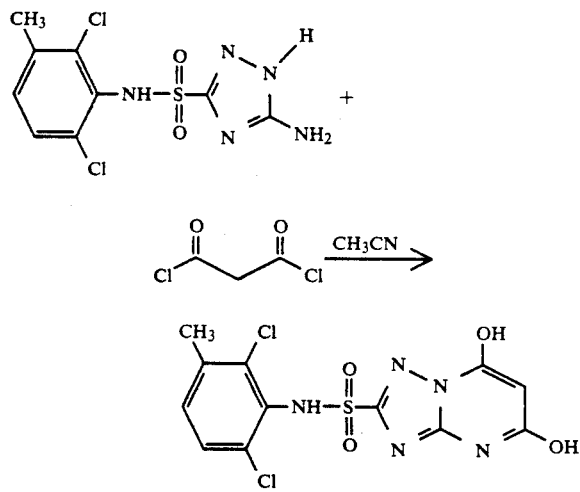

To a stirred solution of 2.52 grams (g) (0.0078 moles) of N-(3-(((2,6-dichloro-3-methylphenyl)amino)sulfonyl)-1H-1,2,4-triazol-5-yl)amine in 100 milliliters (mL) of dry acetonitrile under nitrogen was added 1.5 g (0.01 moles) of freshly distilled malonyl chloride. The mixture was stirred at ambient temperature overnight (14 hr) and a yellow precipitate formed. The solid product was collected by filtration and dried; mp 280°–282° C. (decomposes). The filtrate was found to contain additional product which was recovered by concentrating the filtrate to dryness. The combined yield of product was 2.58 g (85 percent yield).

EXAMPLE 2

Preparation of 5,7-Dichloro-N-(4-bromo-3-methylphenyl)-1,2,4-triazolo[1,5-a]pyrimidine-2-sulfonamide

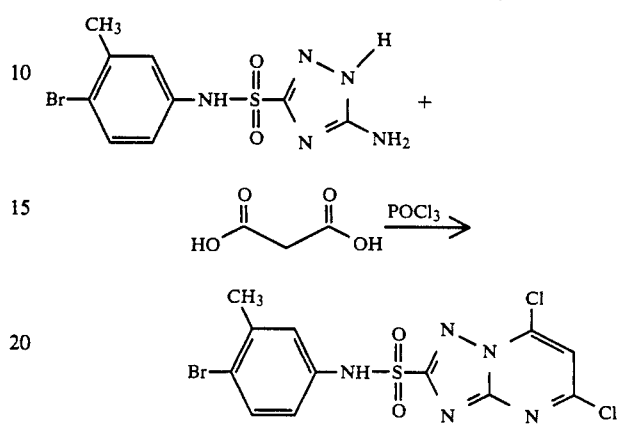

A 3-necked flask equipped with a mechanical stirrer and a reflux condenser was charged with 6.62 g (0.02 moles) of N-(3-(((4-bromo-3-methylphenyl)amino)sulfonyl)-1H-1,2,4-triazol-5-yl)amine, 2.08 g (0.02 moles) of malonic acid and 20 mL (0.21 moles) of phosphorus oxychloride. The mixture was stirred and heated in an oil bath at about 90° C. for 24 hr. The mixture was allowed to cool and was poured into ice-water. The resulting solid product was collected by filtration and dried to give 8.4 g (96 percent yield) of light brown solid having an estimated purity of about 85 to 88 percent. Approximately 7 g of the product was slurried in 50 mL of hot o-dichlorobenzene and residual solids were removed by filtration. Upon cooling, the filtrate provided 5.2 g of product as an orange solid; mp 232°–234° C. (decomposes).

EXAMPLE 3

Preparation of 5,7-Dichloro-N-(2,6-dichloro-3-methylphenyl)-1,2,4-triazolo[1,5-a]pyrimidine-2-sulfonamide

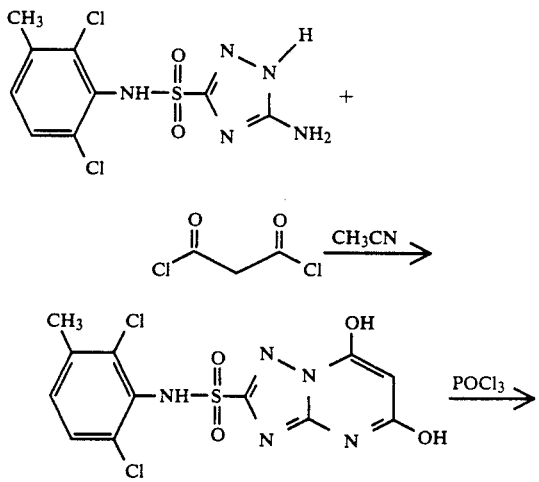

-continued

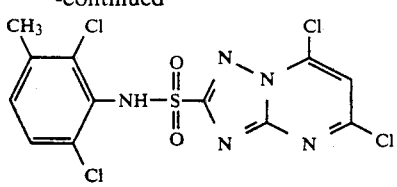

To a stirred solution of 6.44 g (0.02 moles) of N-(3-(((2,6-dichloro-3-methylphenyl)amino)sulfonyl)-1H-1,2,4-triazol-5-yl)amine in 100 mL of dry acetonitrile was added 2.82 g (0.02 moles) of freshly distilled malonyl chloride. The mixture was stirred at room temperature overnight after which time some starting material remained. Additional malonyl chloride (0.56 g) was added and stirring was continued for 4 hrs. The reaction mixture was concentrated to dryness and the residue was slurried with $POCl_3$ (122 g; 0.8 moles) and heated at 90° C. for 9 hrs. The reaction mixture was cooled and concentrated under reduced pressure and the residue was poured into ice-water. The resulting precipitate was filtered and dried to give 8.35 g of product having a purity of 75 percent (73 percent yield).

EXAMPLE 4

Preparation of 5,7-Dichloro-N-(3-methylphenyl)-1,2,4-triazolo[1,5-a]pyrimidine-2-sulfonamide

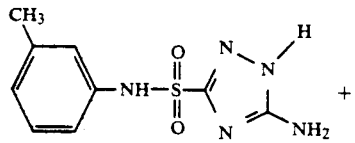

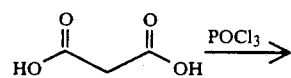

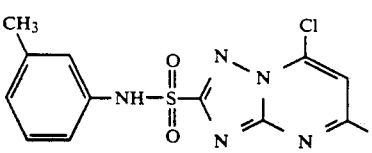

A mixture of 19.9 g (0.075 moles) of N-(3-(((3-methylphenyl)amino)sulfonyl)-1H-1,2,4-triazol-5-yl)amine, 7.9 g (0.075 moles) of malonic acid and 115 g of phosphorus oxychloride were stirred at 60° to 70° C. for 15 hr. HPLC analysis indicated only 55 percent conversion to the desired product. An additional 0.5 g of malonic acid, 20 g of $POCl_3$ and 0.5 g of dimethylaniline as a catalyst were added, and stirring and heating were continued until the reaction was complete. About 50 mL of o-xylene were added as a chaser and approximately 115 g of $POCl_3$ were recovered by distillation at 70° to 80° C. under reduced pressure. After cooling, the desired product was recovered from the o-xylene in a 70 percent yield.

EXAMPLE 5

Preparation of 5,7-Dichloro-N-(2,6-dichloro-3-methylphenyl)-1,2,4-triazolo[1,5-a]pyrimidine-2-sulfonamide

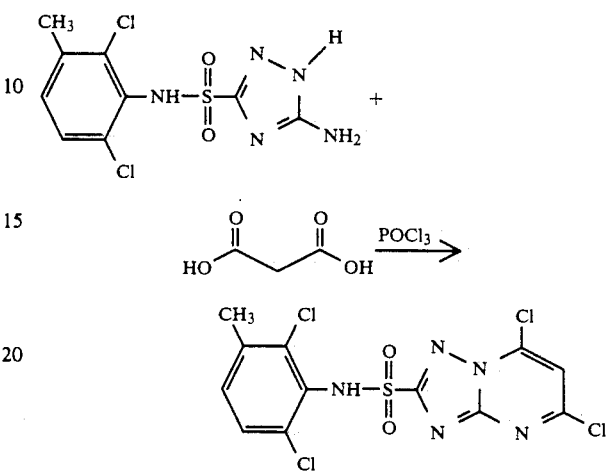

A mixture of 6.44 g (0.02 moles) of N-(3-(((2,6-dichloro-3-methylphenyl)amino)sulfonyl)-1H-1,2,4-triazol-5-yl)amine, 2.1 g (0.02 moles) of malonic acid and 122 g (0.8 moles) of $POCl_3$ were stirred at 90° C. for 24 hrs. The reaction mixture was cooled and concentrated under reduced pressure and the residue was poured into ice-water. The resulting precipitate was filtered and dried to give 7.85 g of product having a purity of 88 percent (81 percent yield).

What is claimed is:

1. A process for the preparation of an N-(aryl)-5,7-dihydroxy-1,2,4-triazolo[1,5-a]pyrimidine-2-sulfonamide of the formula

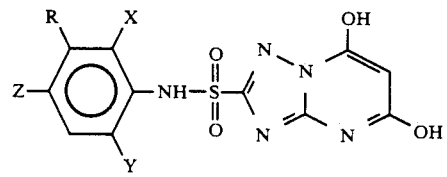

wherein
X represents H, F, Cl, Br, lower alkyl or lower alkoxy,
Y represents H, F, Cl, Br, $CF_3$ or $NO_2$,
R represents H, lower alkyl or lower alkoxy, and
Z represents H, Cl or Br,
consisting essentially of contacting an N-(3-(((aryl)amino)sulfonyl)-1H-1,2,4-triazol-5-yl)amine of the formula:

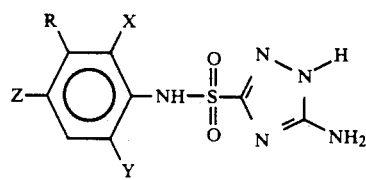

wherein
X, Y, R and Z are as previously defined, with a malonyl halide in a polar aprotic solvent in the presence of the acid generated during the course of the reaction.

2. The process of claim 1 in which X and Y are H, F, or Cl, Z is H or Br, and R is $CH_3$.

3. The process of claim 1 in which the polar aprotic solvent is an alkylnitrile, an ether or a carboxylic acid ester.

4. The process of claim 1 in which the temperature is maintained between ambient temperature and about 100° C.

5. The process of claim 1 which comprises the additional step of converting the N-aryl-5,7-dihydroxy-1,2,4-triazolo-[1,5-a]pyrimidine-2-sulfonamide to the corresponding 5,7-dihalo compound by directly contacting the reaction mixture with a phosphorus oxyhalide.

6. A process for the preparation of an N-(aryl)-5,7-dihalo-1,2,4-triazolo[1,5-a]pyrimidine-2-sulfonamide of the formula

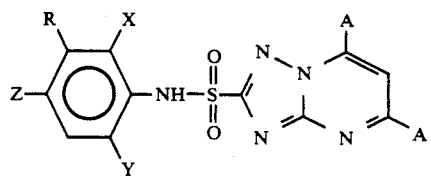

wherein

A represents Cl or Br,
X represents H, F, Cl, Br or lower alkyl,
Y represents H, F, Cl, Br or $NO_2$,
R represents H, lower alkyl or lower alkoxy, and
Z represents H, Cl or Br, consisting essentially of contacting an N-(3-(((aryl)amino)sulfonyl)-1H-1,2,4-triazol-5-yl)amine of the formula:

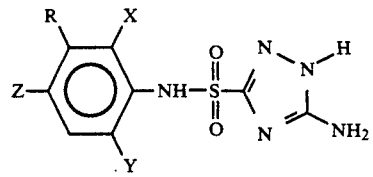

wherein

X, Y, R and Z are as previously defined, with at least one equivalent of malonic acid and at least 4 equivalents of a phosphorus oxyhalide in the presence of the acid generated during the course of the reaction.

7. The process of claim 6 in which A is Cl and the phosphorus oxyhalide is $POCl_3$.

8. The process of claim 7 in which X and Y are H, F or Cl, Z is H or Br, and R is $CH_3$.

9. The process of claim 7 in which $POCl_3$ in excess is used as the solvent.

10. The process of claim 7 in which the temperature is maintained between about 70° and 100° C.

* * * * *